United States Patent

Ahond et al.

[11] Patent Number: 5,481,010
[45] Date of Patent: Jan. 2, 1996

[54] 7-DEACETOXY BECCATINE IV DERIVATIVE AND PREPARATION AND USE THEREOF

[75] Inventors: Alain Ahond, Malakoff; Laurent Ettouati, Rouen; Pierre Potier, Paris; Christiane Poupat, Plaisir, all of France

[73] Assignee: Centre National de la Recherche Scientifique, Paris, France

[21] Appl. No.: 178,322

[22] PCT Filed: July 16, 1991

[86] PCT No.: PCT/JP93/01572

§ 371 Date: Jan. 14, 1994

§ 102(e) Date: Jan. 14, 1994

[87] PCT Pub. No.: WO/03/02064

PCT Pub. Date: Feb. 4, 1993

[51] Int. Cl.⁶ .................................................. C07D 407/04
[52] U.S. Cl. ............................................ 549/432; 549/510
[58] Field of Search ...................................... 549/432, 510

[56] References Cited

U.S. PATENT DOCUMENTS 4,924,012  5/1990  Colin et al. ............................... 549/510

Primary Examiner—Nicky Chan
Attorney, Agent, or Firm—Finnegan, Henderson, Farabow, Garrett & Dunner

[57] ABSTRACT

This invention relates to a novel 7-deacetoxy baccatine IV derivative having formula (I):

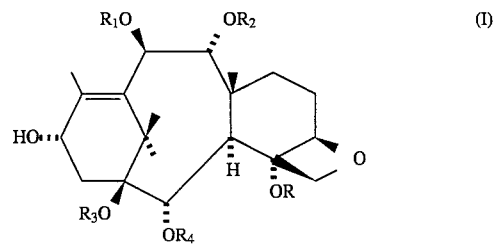

the preparation thereof from taxine B, and its use in preparing biologically active products. In said formula (I), R is a hydrogen atom or acetyl radical and $R_1$, $R_2$, $R_3$, and $R_4$ are hydroxy-function protective groupings (preferably acetonides).

2 Claims, No Drawings

7-DEACETOXY BECCATINE IV DERIVATIVE AND PREPARATION AND USE THEREOF

This application is a 371 of PCT/FR91/00585 filed Jul. 16, 1991.

DESCRIPTION OF THE INVENTION

The present invention relates to a novel 7-deacetoxybaccatin IV derivative of general formula:

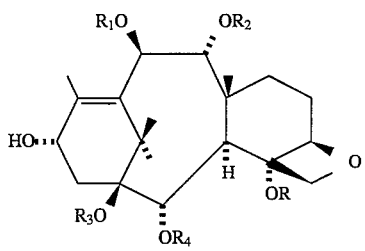

in which R represents a hydrogen atom or an acetyl radical and the $R_1$, $R_2$, $R_3$ and $R_4$ symbols represent protective groups of the hydroxyl functional group, to its preparation and to its use in the preparation of therapeutically active taxane derivatives.

The taxane derivatives of general formula:

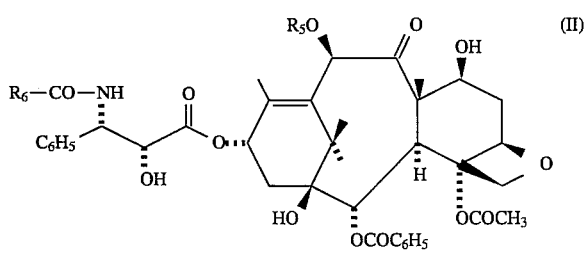

in which $R_5$ represents a hydrogen atom or an acetyl radical and $R_6$ represents a t-butoxy or phenyl radical have notable antitumoral and antileukaemic properties.

The product of general formula (II) in which $R_5$ represents an acetyl radical and $R_6$ represents a phenyl radical, known under the name of taxol, and the product of general formula (II) in which $R_5$ represents a hydrogen atom and $R_6$ represents a t-butoxy radical are described in European Patent EP 0,253,738.

From American Patents U.S. Pat. Nos. 4,924,011 and U.S. Pat. No. 4,924,012, it is known to prepare the products of general formula (II) by esterification of baccatin III or 10-deacetylbaccatin III of formula:

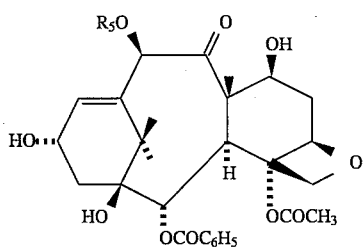

in which $R_5$ is defined as above, using a suitably substituted β-phenylglycidic acid, under suitable conditions.

Baccatin III, and more particularly 10-deacetylbaccatin III, can be extracted from yew (*Taxus baccata*) leaves. The content of these products remains relatively low, although very markedly more significant than that of taxol; moreover, the latter is found essentially in the bark of the trunk.

It is also known that it is possible to extract many alkaloids from the leaves of various yew varieties, the major constituent of which alkaloids is taxine B of formula:

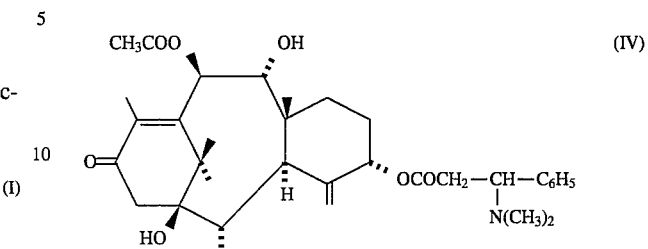

Studies carried out on taxol and its derivatives have made it possible to show, in particular, that the presence of the oxetane ring in the 4,5-position of the taxane skeleton is an essential component for displaying biological activity. It results therefrom that the introduction of an oxetane ring into taxine B, by replacement of the (4,20) exo methylene group and of the ester functional group in the 5-position, can lead to the formation of intermediates which are particularly advantageous for the preparation of taxol or of its derivatives or analogous compounds possessing biological activity.

The subject of the present invention is the product of general formula (I) and its preparation from taxine B.

More particularly, the subject of the present invention is the product of general formula (I) in which the alcohol functional groups in the 1,2-positions, on the one hand, and in the 9,10-positions, on the other hand, are protected in the form of acetonides; in this product of general formula:

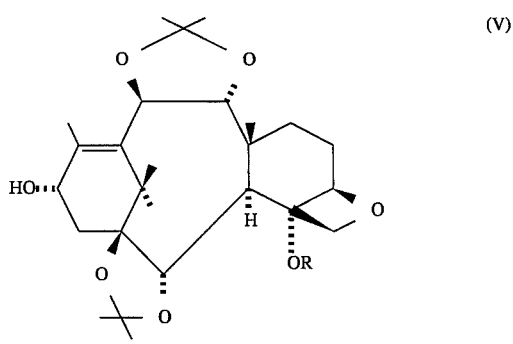

R represents a hydrogen atom or the acetyl radical.

According to the invention, the product of general formula (I), and more particularly the product of general formula (V), can be obtained from taxine B by carrying out, after conversion according to known methods of taxine B to triacetylcinnamoyltaxicin-I of formula:

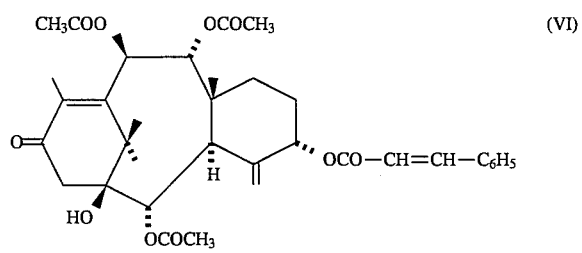

the following sequence of stages:

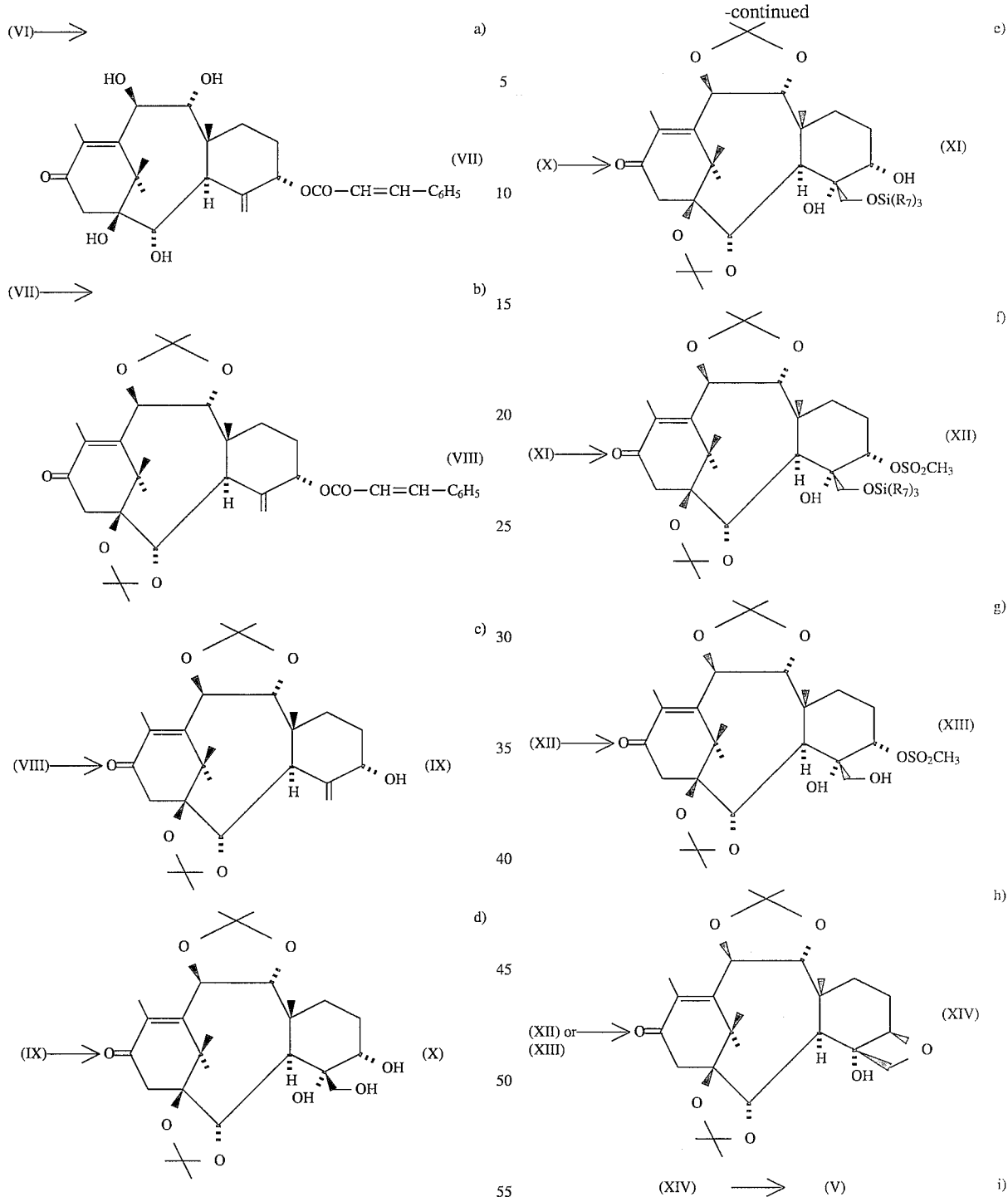

According to the present invention, triacetylcinnamoyltaxicin-I of general formula (VI) is obtained from the crude extract of yew leaves containing essentially taxine B, after quaternization using, for example, methyl iodide and deamination in basic medium, and by acetylation followed by chromatographic separation.

Triacetylcinnamoyltaxicin-I of formula (VI) is converted to 5α-cinnamoyltaxicin-I of formula (VII) by solvolysis in basic medium. Generally, an alkali metal alkoxide such as sodium methoxide in the corresponding alcohol such as methanol, optionally in the presence of a second anhydrous organic solvent such as methylene chloride, is used. It is particularly advantageous to use a 0.1N solution of sodium methoxide in methanol.

Deacetylation can also be carried out using an alkali metal cyanide such as potassium cyanide.

Protection of the hydroxyl functional groups of the product of formula (VII) in the form of acetonides in order to obtain the product of formula (VIII) is preferably carried out using acetone in the presence of an acid catalyst such as concentrated sulphuric acid. Good results are also obtained by using 2,2-dimethoxypropane in the presence of p-toluenesulphonic acid.

The product of formula (IX) is obtained by removing the cinnamoyl group from the product of formula (VIII) using a base. It is particularly advantageous to use a concentrated alkali metal hydroxide solution, such as 20N sodium hydroxide solution, in an organic solvent such as tetrahydrofuran.

The product of formula (X) can be obtained by dihydroxylation of the product of formula (IX) under the conditions described by V. Van Rheenen et al., Tetrahedron Letters, 1973–1976 (1976), using tetrahydrofuran in place of acetone as cosolvent and using a larger amount of osmium tetroxide and of N-methylmorpholine N-oxide as secondary oxidizing agent.

Protection of the primary alcohol functional group of the product of formula (X) in order to obtain the product of general formula (XI), in which the $R_7$ symbols, which are identical or different, each represent an alkyl radical containing 1 to 4 carbon atoms, is generally carried out by reacting a halotrialkylsilane with the product of formula (X), the reaction being carried out in an organic solvent such as dimethylformamide in the presence of an acid acceptor such as imidazole. It is particularly advantageous to use tert-butyldimethylsilyl chloride which makes possible selective protection. Moreover, the tert-butyldimethylsilyl protective group can be more easily removed by fluoride ions in the presence of acetonides.

The product of general formula (XI), in which $R_7$ is defined as above, is converted to a mesylated product of general formula (XII) using, for example, an excess of mesyl chloride in pyridine.

The product of formula (XIII) is generally obtained by reacting a fluoride, such as tetrabutylammonium fluoride, with the product of general formula (XII). It is particularly advantageous to carry out the reaction in an inert organic solvent such as tetrahydrofuran at a temperature in the region of 20° C.

The product of formula (XIV) can be obtained either from the product of formula (XIII) or directly from the product of general formula (XII).

Generally, conversion of the product of formula (XIII) to the product of formula (XIV) is carried out using tetrabutylammonium acetate in butanone at the reflux temperature of the reaction mixture.

Conversion of the product of formula (XII) to the product of formula (XIV) can be carried out using tetrabutylammonium fluoride in an organic solvent such as tetrahydrofuran at the reflux temperature of the reaction mixture.

The product of formula (XIV), the tertiary alcohol functional group of which is optionally acetylated, can be stereoselectively reduced to the product of general formula (V). Generally, the reduction is carried out using diisobutylaluminium hydride, the reaction being carried out in an anhydrous organic solvent such as toluene at a temperature in the region of 0° C.

The product of general formula (I), and more particularly the product of general formula (V), can be converted to precursors, for example of the product of general formula (II), after having carried out a set of reactions, the result of which will have the effect of having:

esterified the 13α-hydroxyl functional group, removed the protective groups of the hydroxyl functional groups in the 1, 2, 9 and 10 positions, oxidized the 9α-hydroxyl functional group, introduced a 7α-hydroxyl functional group, benzoylated the 2α-hydroxyl functional group.

EXAMPLES

The following examples show how the invention can be put into practice.

EXAMPLE 1

Preparation of 2α,9α,10β-triacetyl-5α-cinnamoyltaxicin-I 1) 28 kg of powdered foliated yew stems are treated with 13.5 liters of aqueous ammonia and then placed in 2 macerators. Methylene chloride is then added. Each day, for 10 days, the macerators are emptied and methylene chloride added.

The methylene chloride is concentrated to a final volume of 80 liters. The alkaloids are selectively extracted with 175 liters of 2% (w/v) hydrochloric acid. The acidic aqueous phase is washed with 75 liters of hexane, basified with 3.6 liters of concentrated aqueous ammonia and then extracted with 80 liters of methylene chloride. After drying the methylene chloride solution over 200 g of sodium sulphate, filtering and concentrating to dryness, there are obtained 192 g of an amorphous yellowish powder consisting of the total alkaloids. The yield is 6.86 g of total alkaloids per kilogram of dry plant.

2) A solution of 26 g of total alkaloids in 80 cm$^3$ of tetrahydrofuran is introduced into a 250 cm$^3$ round-bottomed flask equipped with a stirrer and then 15 cm$^3$ of methyl iodide are added dropwise. After stirring for 5 hours at a temperature in the region of 20° C., the solvent is removed under reduced pressure. There are thus obtained 32.5 g of a yellowish powder.

3) The powder obtained above is dissolved in 250 cm$^3$ of absolute ethanol and then the solution is added dropwise, over 1 hour, at 20° C., to 350 cm$^3$ of a 2% (w/v) aqueous potassium carbonate solution. A yellow precipitate is formed which dissolves. After stirring for 3 hours, the ethanol is removed by concentrating and extraction is then carried out with 6 times 100 cm$^3$ of methylene chloride. After drying the organic extracts over magnesium sulphate, filtration and concentration to dryness, 23 g of a yellow powder are obtained.

4) The powder thus obtained is dissolved in 50 cm$^3$ of anhydrous pyridine and 30 cm$^3$ of acetic anhydride at 20° C. After reacting for 3 days, 40 cm$^3$ of absolute ethanol are added at 0° C. and the mixture is then concentrated to dryness.

The residue is taken up in 150 cm³ of ethyl acetate. The solution is washed with 3 times 100 cm³ of 0.25N hydrochloric acid and then with 100 cm³ of distilled water. After drying over magnesium sulphate, filtration and concentration to dryness, 24 g of powder are obtained.

22 g of the powder thus obtained, adsorbed on 100 g of silica (60–200 μm), are chromatographed on a silica column (40–60 μm; diameter 10 cm; height 17 cm), elution being carried out with a heptane/ethyl acetate (6/4 by volume) mixture. After separation of 2 g of taxinine, there are obtained 11.5 g of 2α,9α,10β-triacetyl- 5α-cinnamoyltaxicin-I with a yield of 52%, the characteristics of which are identical to those described by J. N. Baxter et al., J. Chem. Soc., 2964–2971 (1962).

Preparation of 5α-cinnamoyltaxicin-I 5α-Cinnamoyltaxicin-I can be prepared according to one of the following methods:

1) 26 mg of sodium methoxide in methanol (0.05N) are added at 0° C. to 57 mg (0.09 mol) of 2α,9α,10α-triacetyl-5α-cinnamoyltaxicin-I dissolved in 5 cm³ of methanol and 1 cm³ of methylene chloride. After reacting for 6 hours 30 minutes, the mixture is neutralized by addition of 0.1N hydrochloric acid. After concentration, extraction with ethyl acetate and washing with distilled water, the organic phase is dried over magnesium sulphate. After concentration, the product obtained is chromatographed on a plate of silica gel in a methylene chloride/methanol (95/5 by volume) mixture. There are thus obtained 18.2 mg of 5α-cinnamoyltaxicin-I, the characteristics of which are identical to those described by J. N. Baxter et al., J. Chem. Soc., 2964–2971 (1962). The yield is 41%.

2) 229 mg of sodium methoxide are added at 0° C. to 8 g of 2α,9α,10β-triacetyl-5α-cinnamoyltaxicin-I in 17.5 cm³ of methylene chloride and 25 cm³ of methanol. After reacting for 50 hours, the mixture is neutralized with 0.1N hydrochloric acid. After concentration under reduced pressure, extraction with ethyl acetate, washing with distilled water, drying over magnesium sulphate and filtration, the organic phase is concentrated to dryness. After chromatography on silica, the eluent being a heptane/ethyl acetate (6/4 by volume) mixture, there are obtained 4 g of 5α-cinnamoyltaxicin-I. The yield is 62%.

3) 165 mg of potassium cyanide are added to 2.5 g of 2α,9α,10β-triacetyl-55α-cinnamoyltaxicin-I in solution in 5 cm³ of methanol and 2 cm³ of methylene chloride. After stirring for 4 days at 20° C., 170 mg of potassium cyanide are added.

After stirring for 6 days, the reaction mixture is concentrated and then extracted with an ethyl acetate/water mixture. After separating by settling, the organic phase is washed with distilled water and then dried over magnesium sulphate. After filtration and concentration, the residue is chromatographed on silica, the eluent being a heptane/ethyl acetate (6/4 by volume) mixture. There are thus obtained 934 mg of 5α-cinnamoyltaxicin-I. The yield is 47%.

EXAMPLE 3

Selective protection of the hydroxyl functional groups

The reaction is carried out according to one of the following methods:

1) 12 drops of concentrated sulphuric acid are added at 0° C. to 4 g of 5α-cinnamoyltaxicin-I in 12 cm³ of distilled acetone. After reacting for 48 hours at 0° C., 25 cm³ of a saturated aqueous sodium bicarbonate solution are added. After extraction with methylene chloride, the organic phases are washed with water and then dried over magnesium sulphate. After filtration and concentration to dryness, the residue is chromatographed on silica, the eluent being a heptane/ethyl acetate (9/1 by volume) mixture. There are thus obtained 3.2 g of the product of formula (VII), the characteristics of which are the following:

melting point: 148°–150° C. (ethanol)

optical rotation: $[\alpha]_D = +204°$ (c=0.84, ethanol)

The structure of the product obtained is confirmed by the mass spectrum (chemical ionization), the infrared spectrum and the proton nuclear magnetic resonance spectrum.

2) A catalytic amount of p-toluenesulphonic acid is added to 42 mg of 5α-cinnamoyltaxicin-I in 1 cm³ of 2,2-dimethoxypropane. After reacting for 8 days, the reaction mixture is diluted with a 5% aqueous sodium bicarbonate solution. After extraction with ethyl acetate, the organic phase is washed with distilled water and then dried over magnesium sulphate. After filtration and concentration, the residue is treated on a plate of silica gel in methylene chloride. There are thus obtained 29 mg of the product of formula (VIII).

EXAMPLE 4

Basic hydrolysis of the product of formula (VIII)

751 mg of the product of formula (VIII) are dissolved in 12 cm³ of tetrahydrofuran and 4 cm³ of 20N sodium hydroxide solution. The mixture is heated at reflux for 4 days. After cooling, the reaction mixture is diluted with distilled water and then extracted with methylene chloride. The organic phase is washed several times with an aqueous sodium chloride solution and then dried over sodium sulphate. After filtration and concentration to dryness, there are obtained 568 mg of the product of formula (IX), the characteristics of which are the following:

melting point: 254°–256° C. (ethanol)

optical rotation: $[\alpha]_D = +241°$ (c=1.42, chloroform)

ultraviolet spectrum: $\lambda_{max} = 272$ nm, $\epsilon = 3300$ (ethanol)

The structure of the product obtained is confirmed by the infrared spectrum, the mass spectrum (chemical ionization) and the proton and $^{13}C$ nuclear magnetic resonance spectra.

EXAMPLE 5

Dihydroxylation of the product of formula (IX)

608 mg of the product of formula (IX) are dissolved in 8 cm³ of tetrahydrofuran and 4 cm³ of water. 2.39 g of N-methylmorpholine N-oxide and 1.15 cm³ of a 2% (w/v) solution of osmium tetroxide in t-butanol are then added. The solution becomes reddish. After reacting for 19 hours, 400 mg of Florisil, 5 cm³ of water and 50 mg of sodium dithionite are added. After stirring for 10 minutes, the mixture is filtered through sintered glass and the filtrate then neutralized by addition of 0.1N hydrochloric acid. After concentration under reduced pressure, the mixture is acidified to pH=4, saturated with sodium chloride and then extracted with ethyl acetate. After drying the organic phase and concentration to dryness, the residue is chromatographed on silica, the eluent being a heptane/ethyl acetate (6/4 by volume) mixture. There are obtained, with a yield of 81%, 530 mg of product of formula (X), the characteristics of which are the following:

melting point: 102°–104° C. (ether/heptane)

optical rotation: $[\alpha]_D = +8.5°$ (c=1.62, chloroform)

The structure of the product obtained is confirmed by the infrared spectrum, the mass spectrum (chemical ionization) and the proton nuclear magnetic resonance spectrum.

EXAMPLE 6

Protection of the primary alcohol functional group of the product of formula (X)

644 mg of imidazole and 586 mg of tert-butyldimethylsilyl chloride are dissolved in 5 cm³ of dimethylformamide. After 15 minutes, 336 mg of the product of formula (X) are added. After reacting for 16 hours, the reaction mixture is poured onto crushed ice. The precipitate formed is separated, washed with distilled water and then taken up in ethyl acetate. The organic phase is dried over magnesium sulphate. After filtration and concentration to dryness, there are obtained 422 mg of product of formula (XI) in which two of the $R_7$ symbols represent a methyl radical and the third a tert-butyl radical, the characteristics of which are the following:

melting point: 178°–180° C. (ethanol)

optical rotation: $[\alpha]_D=+188°$ (c=0.47, chloroform)

The structure of the product obtained is confirmed by the infrared spectrum, the mass spectrum (electron impact) and the proton nuclear magnetic resonance spectrum.

The yield is in the region of 100%.

EXAMPLE 7

Mesylation of the product of formula (XI)

0.25 cm³ of methanesulphonyl chloride is added dropwise, at 0° C., to a solution of 422 mg of the product of formula (XI) obtained in Example 6 in 10 cm³ of pyridine and then the temperature is allowed to return to about 20° C. After reacting for 17 hours, 70 cm³ of methylene chloride are added. The organic phase, separated by settling, is washed with a 0.01N hydrochloric acid solution and then with a saturated sodium bicarbonate solution and finally dried over magnesium sulphate. After filtration and evaporation of the solvent, there are obtained, with a yield of 88%, 421 mg of the product of formula (XII) in which $R_7$ is defined as in Example 6, the characteristics of which are the following:

amorphous powder optical rotation: $[\alpha]_D=+186°$ (c=1.48, chloroform)

The structure of the product obtained is confirmed by the infrared spectrum, the mass spectrum (electron impact) and the proton nuclear magnetic resonance spectrum.

EXAMPLE 8

Deprotection of the product of formula (XII)

237 mg of tetrabutylammonium fluoride trihydrate are added at a temperature of 20° C. to a solution of 421 mg of the product of formula (XII) in 5 cm³ of tetrahydrofuran. After reacting for 1 hour, the reaction mixture is diluted with ethyl acetate and then washed with a saturated sodium bicarbonate solution. The organic phase is dried over magnesium sulphate. After filtration and evaporation of the solvent, the residue is chromatographed on silica, the eluent being a heptane/ethyl acetate (5/5 by volume) mixture. There are thus obtained, with a yield of 88%, 308 mg of product of formula (XIII), the characteristics of which are the following:

amorphous powder optical rotation: $[\alpha]_D=+243°$ (c=1.08, chloroform)

The structure of the product obtained is confirmed by the infrared spectrum, the mass spectrum (chemical ionization) and the proton nuclear magnetic resonance spectrum).

EXAMPLE 9

Preparation of the product of formula (XIV) from the product of formula (XIII)

158 mg of tetrabutylammonium acetate are added to a solution of 29 mg of the product of formula (XIII) in 1 cm³ of butanone. After reacting for 19 hours, ethyl acetate is added. The organic solution is washed with a 0.1N hydrochloric acid solution and then with a saturated sodium chloride solution and finally dried over magnesium sulphate. After filtration and concentration to dryness, there are obtained, with a yield of 80%, 19.3 mg of the product of formula (XIV), the characteristics of which are the following:

amorphous powder optical rotation: $[\alpha]_D=+213°$ (c=0.76, chloroform)

The structure of the product obtained is confirmed by the infrared spectrum, the mass spectrum (chemical ionization, electron impact) and the proton and $^{13}C$ nuclear magnetic resonance spectra.

EXAMPLE 10

Preparation of the product of formula (XIV) from the product of formula (XII)

10.6 mg of the product of formula (XII) are dissolved in 1 cm³ of tetrahydrofuran and then 20 mg of tetrabutylammonium fluoride are added at reflux. After reacting for 15 hours, ethyl acetate is added. The organic phase is washed with distilled water and then dried over magnesium sulphate. After filtration and evaporation of the solvent, the residue is treated on a preparative silica gel plate in the hexane/ethyl acetate (6/4 by volume) mixture. There are thus obtained, with a yield of 22%, 1.6 mg of product of formula (XIV), the characteristics of which are identical to those of the product obtained in Example 9.

EXAMPLE 11

Selective reduction of the product of formula (XIV)

0.4 cm³ of a 1M solution of diisobutylaluminium hydride in toluene is added, at 0° C., under an argon atmosphere, to 36.5 mg of product of formula (XIV) in solution in 1 cm³ of toluene. After 1 hour, methanol is added dropwise and the mixture is then stirred for 15 minutes. After filtration and evaporation of the solvent, the residue is treated by chromatography on a preparative silica gel plate in the heptane/ethyl acetate (6/4 by volume) mixture. There are thus obtained, with a yield of 39%, 14.3 mg of product of formula (V), the characteristics of which are the following:

amorphous powder optical rotation: $[\alpha]_D=+88°$ (c=0.1, chloroform)

infrared spectrum: characteristic bands at 3444, 1381, 1375, 1237 and 1050 cm$^{-1}$ mass spectrum (chemical ionization) (T=190° C.) m/z: 447 (MH$^+$-H$_2$O) , 407 (MH$^+$-acetone) , 389 (447-acetone) , 371 (389-H$_2$O), 331 (389-acetone), 313 (331-H$_2$O)

proton nuclear magnetic resonance spectrum (400 MHz; deuterated chloroform):

| | | | | |
|---|---|---|---|---|
| dd | (J = 8 and 4 Hz) | 1H | 4.80 | $C_5$—H |
| d | (J = 9 Hz) | 1H | 4.63 | $C_{10}$—H |
| d | (J = 8 Hz) | 1H | 4.60 | $C_{20}$—H |
| br.d | (J = 10 Hz) | 1H | 4.47 | $C_{13}$—H |
| d | (J = 8 Hz) | 1H | 4.35 | $C_{20}$—H |
| d | (J = 9 Hz) | 1H | 4.12 | $C_9$—H |
| d | (J = 5 Hz) | 1H | 4.10 | $C_2$—H |
| dd | (J = 16 and 10 Hz) | 1H | 2.50 | $C_{14}$—H |
| dd | (J = 16 and 3 Hz) | 1H | 2.17 | $C_{14}$—H |

-continued

| | | | | |
|---|---|---|---|---|
| d | (J = 5 Hz) | 1H | 2.12 | $C_3$—H |
| m | | 2H | 2.00 | $C_6$—H and $C_7$—H |
| d | (J = 1 Hz) | 3H | 1.93 | $C_{18}$—$H_{(3)}$ |
| s | | 6H | 1.50 | $2CH_3$ |
| s | | 3H | 1.47 | $C_{19}$—$H_{(3)}$ |
| s | | 6H | 1.42 | $2CH_3$ |
| s | | 3H | 1.35 | $C_{16}$—$H_{(3)}$ |
| m | | 1H | 1.30 | $C_7$—H |
| s | | 3H | 1.13 | $C_{17}$—$H_{(3)}$ |

EXAMPLE 12

Acetylation of the product of formula (XIV)

Under the standard acetylation conditions (acetic anhydride/pyridine; 4-dimethylaminopyridine), the product of formula (XIV) is acetylated in the 4position with a yield of 58%.

The product obtained has the following characteristics.

amorphous powder optical rotation: $[\alpha]_D=+229°$ (c=0.38, chloroform)

The structure of the product obtained is confirmed by the infrared spectrum, the mass spectrum (chemical ionization) and the proton nuclear magnetic resonance spectrum.

EXAMPLE 13

Esterification of the product of formula (v)

9 mg of cinnamic acid, 12.6 mg of dicyclohexylcarbodiimide and 2 mg of 4-dimethylaminopyridine are added to a solution of 7.1 mg of product of formula (V) in 0.5 cm³ of methylene chloride. After reacting for 2 hours, the reaction mixture is filtered. The filtrate is washed with a 0.01N hydrochloric acid solution and then with 0.5N sodium hydroxide solution. The organic phase is dried over magnesium sulphate. After filtration and evaporation of the solvent, the residue is treated on a preparative silica gel plate in the heptane/ethyl acetate (7/3 by volume) mixture. There are thus obtained 5.2 mg of the 13α-cinnamoylated derivative of the product of formula (V) with a yield of 57%. The product obtained has the following characteristics:

amorphous powder optical rotation: $[\alpha]_D=+342°$ (c=0.45, chloroform)

The structure of the product obtained is confirmed by the infrared spectrum, the mass spectrum (chemical ionization) and the proton nuclear magnetic resonance spectrum.

We claim:

1. A 7-deacetoxybaccatin IV derivative of formula:

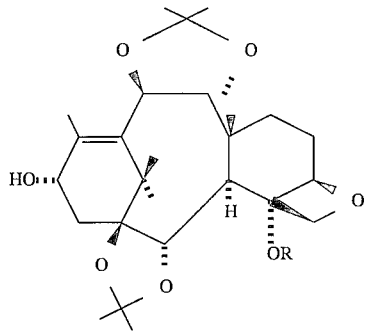

in which R represents a hydrogen atom or an acetyl radical.

2. The product of formula:

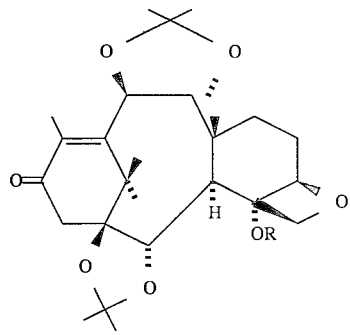

in which R represents a hydrogen atom or the acetyl radical.

* * * * *